United States Patent
Chellamuthu et al.

(10) Patent No.: US 9,840,586 B2
(45) Date of Patent: Dec. 12, 2017

(54) METHODS FOR MEASURING PROPERTIES IN CROSSLINKED POLYCARBONATE

(71) Applicant: SABIC Global Technologies B.V., Bergen op Zoom (NL)

(72) Inventors: Manojkumar Chellamuthu, Evansville, IN (US); Paul Dean Sybert, Evansville, IN (US)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 15/036,552

(22) PCT Filed: Nov. 14, 2014

(86) PCT No.: PCT/US2014/065729
§ 371 (c)(1),
(2) Date: May 13, 2016

(87) PCT Pub. No.: WO2015/073841
PCT Pub. Date: May 21, 2015

(65) Prior Publication Data
US 2016/0289378 A1 Oct. 6, 2016

Related U.S. Application Data

(60) Provisional application No. 61/904,714, filed on Nov. 15, 2013.

(51) Int. Cl.
*G01N 33/44* (2006.01)
*C08G 64/14* (2006.01)
*C08G 64/42* (2006.01)
*C08K 5/00* (2006.01)

(52) U.S. Cl.
CPC ............ *C08G 64/14* (2013.01); *C08G 64/42* (2013.01); *C08K 5/0066* (2013.01); *G01N 33/442* (2013.01)

(58) Field of Classification Search
CPC ..................................................... G01N 33/44
USPC ......................................................... 436/85
See application file for complete search history.

(56) References Cited

U.S. PATENT DOCUMENTS

| | | | |
|---|---|---|---|
| 4,153,780 A | 5/1979 | Narita et al. | |
| 6,353,046 B1 * | 3/2002 | Rosenquist | C08K 5/0066 524/155 |
| 6,780,917 B2 * | 8/2004 | Hashimoto | C08L 69/00 524/442 |
| 6,790,899 B2 * | 9/2004 | Singh | C08K 5/0066 252/400.2 |
| 6,956,073 B2 * | 10/2005 | Takagi | C08K 5/523 524/127 |
| 7,073,309 B2 * | 7/2006 | van Driesten | C09J 7/0217 53/415 |
| 7,511,092 B2 * | 3/2009 | Glasgow | C08K 5/109 524/280 |
| 7,544,745 B2 * | 6/2009 | Ma | C08L 69/00 524/115 |
| 8,314,202 B2 * | 11/2012 | Emrick | C08G 18/10 528/125 |
| 2003/0004251 A1 * | 1/2003 | Hashimoto | C08L 69/00 524/456 |
| 2004/0082691 A1 * | 4/2004 | Singh | C08K 5/0066 524/155 |
| 2004/0191459 A1 * | 9/2004 | Driesten | C09J 7/0217 428/42.2 |
| 2005/0244974 A1 * | 11/2005 | Garcia-Franco | G01N 33/445 436/85 |
| 2007/0082989 A1 * | 4/2007 | Glasgow | C08K 5/109 524/284 |
| 2007/0093591 A1 * | 4/2007 | Ma | C08L 69/00 524/502 |
| 2007/0299174 A1 * | 12/2007 | Chen | C08L 51/04 524/158 |
| 2008/0081860 A1 * | 4/2008 | Li | C08G 64/14 524/414 |
| 2009/0061215 A1 * | 3/2009 | Baumgart | B29C 37/0032 428/336 |
| 2009/0247660 A1 * | 10/2009 | Park | A61K 6/083 522/25 |
| 2011/0112241 A1 * | 5/2011 | Emrick | C08G 18/10 524/549 |
| 2012/0259031 A1 * | 10/2012 | Dake | B29C 67/0066 522/11 |

FOREIGN PATENT DOCUMENTS

EP 0 001 557 A1 5/1979

OTHER PUBLICATIONS

Ishida, H. et al, Journal of Polymer Science B: Polymer Physics 2000, 38, 3289-3301.*
Wang, J. et al, Journal of Applied Polymer Science 2010, 115, 330-337.*

(Continued)

*Primary Examiner* — Arlen Soderquist
(74) *Attorney, Agent, or Firm* — Cantor Colburn LLP

(57) ABSTRACT

Methods for measuring certain properties of a crosslinked polycarbonate are disclosed. The storage modulus of a crosslinked polycarbonate is measured over a specified temperature range, and the average magnitude of the storage modulus over that temperature range is obtained. The average magnitude can be correlated to both crosslinking within the polycarbonate, and to the flame performance of the crosslinked polycarbonate.

11 Claims, 10 Drawing Sheets

(56) References Cited

OTHER PUBLICATIONS

Li, L. et al, Journal of Applied Polymer Science 2012, 124, 3807-3814.*
International Search Report and Written Opinion dated Jan. 22, 2015 from PCT/US2014/065729.

* cited by examiner

METHODS FOR MEASURING PROPERTIES IN CROSSLINKED POLYCARBONATE

BACKGROUND

The present disclosure relates to rheological methods for measuring crosslinking, flame performance, chemical retardance, mechanical properties, or other characteristics of a crosslinked polycarbonate. These methods are particularly useful with polycarbonates that have been crosslinked by exposure to ultraviolet light.

Crosslinking of polymeric chains is a common method for modifying polymers because of its influence on mechanical properties, mobility, solubility, and diffusion. Potential benefits included improved mechanical and thermal properties as well as superior chemical and flame retardance. These attributes are desirable in applications ranging from automotive to telecommunications to consumer electronics and other fields.

Crosslinks can be formed by chemical reactions initiated by, for example, heating or irradiation. Desirably, covalent crosslinking bonds are formed, since such bonds are mechanically and thermally stable, and thus are harder to break. The morphology of the crosslinks can affect the properties and features of the crosslinked polymer. It would be desirable to be able to quantify the amount of crosslinking in a crosslinked polymer, and/or to be able to predict the properties of the crosslinked polymer based on the amount of crosslinking.

BRIEF DESCRIPTION

The present disclosure thus relates to methods by which the amount of crosslinking of a polymer, particularly a polycarbonate, can be measured and the properties predicted therefrom. Dynamic mechanical analysis is used to measure the storage modulus G' of the crosslinked polycarbonate, and an average value for the storage modulus is determined from a specified range in the rubber plateau. The gel thickness and the flame performance of the crosslinked polycarbonate are shown to be correlated to the average value.

Disclosed in various embodiments are methods for determining the flame performance of a crosslinked polycarbonate, comprising: measuring the storage modulus (G') versus temperature of the crosslinked polycarbonate using dynamic mechanical analysis, the measurement including a rubber plateau of the polycarbonate; extrapolating an average magnitude of the storage modulus over a temperature range within the rubber plateau; and determining the flame performance of the crosslinked polycarbonate based on the average magnitude of the storage modulus.

The crosslinked polycarbonate may be a bisphenol-A homopolymer having endcaps derived from 4-hydroxybenzophenone. Alternatively, the crosslinked polycarbonate may be a copolymer having monomers derived from 4,4'-dihydroxybenzophenone.

The flame performance can be determined by comparing the average magnitude of the storage modulus to a reference table. Alternatively, the flame performance can be determined by comparing the average magnitude of the storage modulus to a threshold value. The temperature range may be at least 10° C.

Also described herein are methods for selecting a crosslinkable polycarbonate that will achieve UL94 5VA performance at a thickness of 1.5 mm, comprising: producing a crosslinkable polycarbonate resin that contains an aromatic ketone-containing moiety derived from a dihydroxy compound or a monohydroxy compound; producing a composition containing at least the crosslinkable polycarbonate resin and a flame retardant additive; molding a part from the composition; exposing the molded part to ultraviolet light to induce crosslinking; measuring the storage modulus (G') versus temperature of the molded part using dynamic mechanical analysis, the measurement including a rubber plateau of the polycarbonate; extrapolating an average magnitude of the storage modulus over a temperature range within the rubber plateau; and selecting the polycarbonate resin if the G' is 5 or greater.

The temperature range over which the average magnitude is determined may be at least 10° C., preferably at least 30° C.

Also disclosed are polycarbonate compositions comprising: a flame retardant additive; and at least one crosslinkable polycarbonate resin that contains an aromatic ketone-containing moiety derived from a dihydroxy compound or a monohydroxy compound; wherein an article which is molded from the polycarbonate composition and exposed to ultraviolet light will have an average storage modulus of 5 or greater when averaged over a temperature range of at least 10° C. within the rubber plateau.

The composition can further comprise a non-crosslinkable polycarbonate resin. The composition may have a MFI of 4 to 10 g/10 min as measured at 300° C., 1.2 kg.

In specific embodiments, the average storage modulus is determined by averaging between 160° C. and 190° C.

Sometimes, the molded article can achieve UL94 5VA performance at a thickness of 1.5 mm. The molded article may alternatively be able to achieve UL94 V0 performance at a thickness of 1.2 mm Various embodiments are also disclosed of methods for selecting a crosslinkable polycarbonate that will achieve UL94 V0 performance at a thickness of 1.2 mm, comprising: producing a crosslinkable polycarbonate resin that contains an aromatic ketone-containing moiety derived from a dihydroxy compound or a monohydroxy compound; producing a composition containing at least the crosslinkable polycarbonate resin and a flame retardant additive; molding a part from the composition; exposing the molded part to ultraviolet light to induce crosslinking; measuring the storage modulus (G') versus temperature of the molded part using dynamic mechanical analysis, the measurement including a rubber plateau of the polycarbonate; extrapolating an average magnitude of the storage modulus over a temperature range within the rubber plateau; and selecting the polycarbonate resin if the G' is 9 or greater.

The temperature range over which the average magnitude is determined may be at least 10° C. In particular embodiments, the temperature range over which the average magnitude is determined is 30° C.

These and other non-limiting aspects of the present disclosure are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
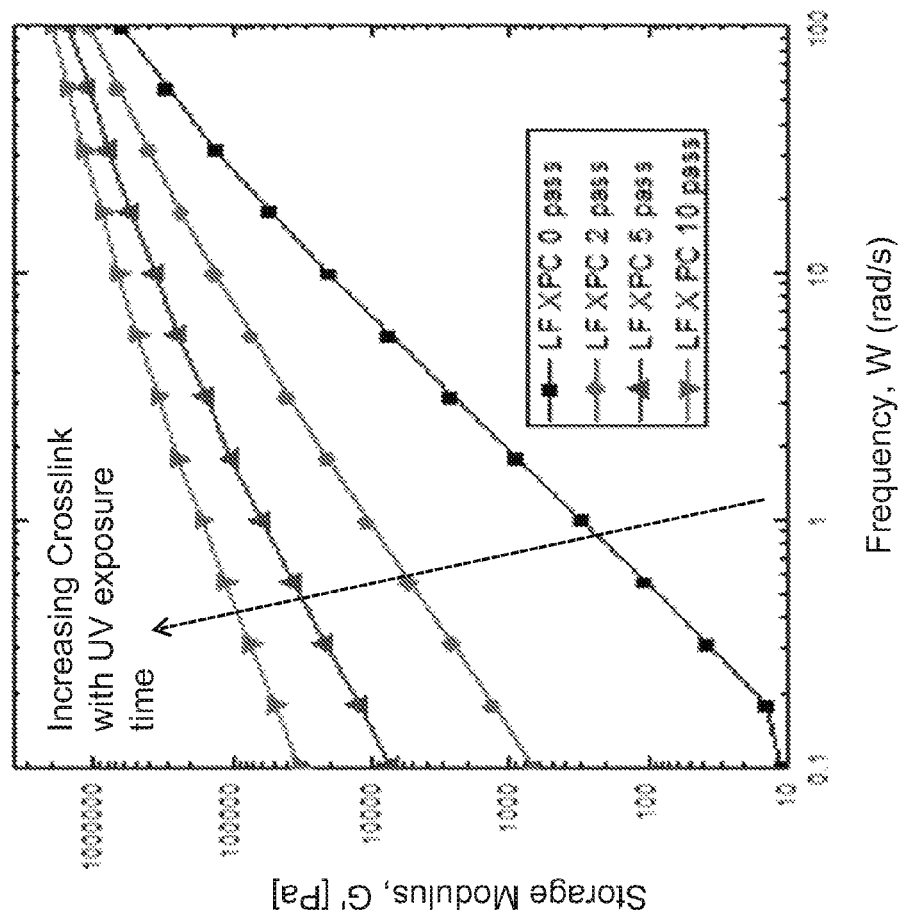
FIG. 1 is a graph of Dynamic Oscillatory Rheology being performed on a series of crosslinked polycarbonate films formed with 3.5 mole % 4-hydroxybenzophenone (4-HBP) end cap and then exposed to UV light for different exposure times. The storage modulus G' is measured versus frequency (rad/sec) at 300° C. This graph indicates that as the UV exposure time increases, the storage modulus increases for a given frequency. Zero passes (non-irradiated) is in squares, 2 passes is in diamonds, 5 passes is with upright triangle, and 10 passes is with inverted triangle.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application, particularly as they relate to polymers or polymer compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

As used herein, approximating language may be applied to modify any quantitative representation that may vary without resulting in a change in the basic function to which it is related. Accordingly, a value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the terms "polycarbonate" and "polycarbonate polymer" mean a polymer having repeating structural carbonate units of the formula (1):

(1)

in which at least about 60 percent of the total number of $R^1$ groups are aromatic organic radicals and the balance thereof are aliphatic, alicyclic, or aromatic radicals. An ester unit (—COO—) is not considered a carbonate unit, and a carbonate unit is not considered an ester unit. In one embodiment, each $R^1$ is an aromatic organic radical, for example a radical of the formula (2):

-$A^1$-$Y^1$-$A^2$-  (2)

wherein each of $A^1$ and $A^2$ is a monocyclic divalent aryl radical and $Y^1$ is a bridging radical having one or two atoms that separate $A^1$ from $A^2$. In an exemplary embodiment, one atom separates $A^1$ from $A^2$. Illustrative non-limiting examples of radicals of this type are —O—, —S—, —S(O)—, —S(O$_2$)—, —C(O)—, methylene, cyclohexyl-methylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ may be a hydrocarbon group or a saturated hydrocarbon group such as methylene, cyclohexylidene, or isopropylidene. The term "polycarbonate" encompasses both homopolycarbonates and copolycarbonates.

Polycarbonates may be produced by the interfacial reaction of dihydroxy compounds having the formula HO—$R^1$—OH, wherein $R^1$ is as defined above. Dihydroxy compounds suitable in an interfacial reaction include the dihydroxy compounds of formula (A) as well as dihydroxy compounds of formula (3)

wherein $Y^1$, $A^1$ and $A^2$ are as described above. Also included are bisphenol compounds of general formula (4):

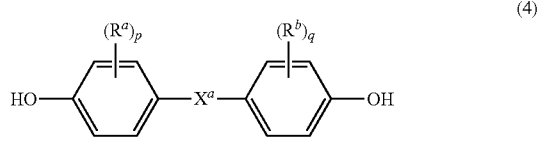

wherein $R^a$ and $R^b$ each represent a halogen atom or a monovalent hydrocarbon group and may be the same or different; p and q are each independently integers of 0 to 4; and $X^a$ represents one of the groups of formula (5):

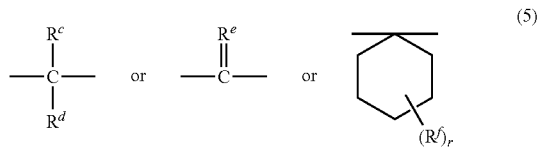

wherein $R^c$ and $R^d$ each independently represent a hydrogen atom or a monovalent linear or cyclic hydrocarbon group; $R^e$ is a divalent hydrocarbon group; $R^f$ is a monovalent linear hydrocarbon group; and r is an integer from 0 to 5.

Specific examples of the types of bisphenol compounds that may be represented by formula (3) include 1,1-bis(4-hydroxyphenyl)methane, 1,1-bis(4-hydroxyphenyl)ethane, 2,2-bis(4-hydroxyphenyl)propane (hereinafter "bisphenol-A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-1-methylphenyl)propane, 1,1-bis(4-hydroxy-t-butylphenyl)propane; 4,4'-(1-phenylethane-1,1-diyl)diphenol or 1,1-bis(4-hydroxyphenyl)-1-phenyl-ethane (bisphenol-AP); 1,1-bis(4-hydroxyphenyl)-3,3,5-trimethylcyclohexane) (bisphenol TMC); 1,1-bis(4-hydroxy-3-methylphenyl)cyclohexane (DMBPC); and 2,2-bis(3,5-dibromo-4-hydroxyphenyl)propane (tetrabromobisphenol-A or TBBPA). Depicted below is bisphenol-A, which is a commonly used monomer in polycarbonates.

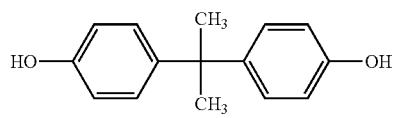

The methods of the present disclosure are used to determine the relative amount of crosslinking that is present in a crosslinked polycarbonate.

Generally, a crosslinkable polycarbonate polymer is provided as a sheet or a film, the polycarbonate containing photoactive moieties that are capable of crosslinking under irradiation at the appropriate wavelength. Generally, such moieties include a double bond, such as a ketone group (—CO—) or a vinyl group (—CH=CH—), which can be broken to permit crosslinking between polymeric chains. Such moieties generally also include one or more reactive groups that can be used to form a covalent bond and join the moiety to a polymeric backbone. Such reactive groups may include a hydroxyl, amino, or carboxyl group.

The term "hydroxyl" refers to a radical of the formula —OH, wherein the oxygen atom is covalently bonded to a carbon atom.

The term "amino" refers to a radical of the formula R—$NH_2$, wherein R is a carbon atom. For purposes of this disclosure, the amino group is a primary amino group, i.e. contains two hydrogen atoms.

The terms "carboxy" or "carboxyl" refers to a radical of the formula —COOH, wherein the carbon atom is covalently bonded to another carbon atom. It should be noted that for the purposes of this disclosure, a carboxyl group may be considered as having a hydroxyl group. However, it should be noted that a carboxyl group can participate in certain reactions differently from a hydroxyl group.

In specific embodiments, the photoactive moieties are provided by a benzophenone. The benzophenone has either one or two phenolic groups, and provides a photoactive ketone group for crosslinking. In some embodiments, the benzophenone is a monohydroxybenzophenone, and has the structure of Formula (I).

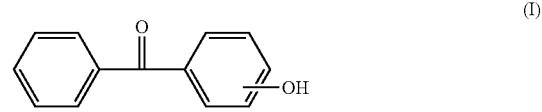

In more specific embodiments, the monohydroxybenzophenone is 4-hydroxybenzophenone (4-HBP).

In other embodiments, the benzophenone is a dihydroxybenzophenone, and has the structure of Formula (II).

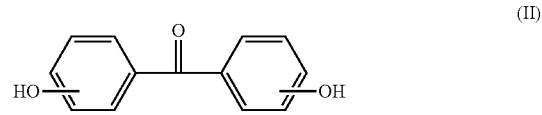

The two hydroxyl groups can be located in any combination of locations, e.g. 4,4'-; 2,2'-; 2,4'-; etc. In more specific embodiments, the dihydroxybenzophenone is 4,4'-dihydroxybenzophenone (4,4'-DHBP).

A crosslinkable polycarbonate can be formed from at least four different processes. Each process includes the following ingredients: a diol, an end-capping agent, a carbonate precursor, a tertiary amine catalyst, water, and a water-immiscible organic solvent, and optionally a branching agent. The polymerization reaction usually occurs under caustic (i.e. basic) conditions. It should be noted that more than one of each ingredient can be used to produce the crosslinkable polycarbonate. Some information on each ingredient is first provided below.

A hydroxybenzophenone is present as the photoactive moiety, and can be present either as the end-capping agent (i.e., monohydroxybenzophenone) or as a diol (i.e. dihydroxybenzophenone). In the process descriptions below, reference will be made to diols, which should be construed as including a dihydroxybenzophenone monomer as well as other diol monomers. Reference will also be made to the end-capping agent, which should be construed as including a monohydroxybenzophenone.

The diol has two hydroxyl groups, and can include monomers of Formulas (3) or (4) as described above. Bisphenol-A is an example of a diol, as well as 4,4'-dihydroxybenzophenone (4,4'-DHBP). More than one diol can be used, resulting in a copolycarbonate.

Examples of end-capping agents (other than the monohydroxybenzophenone) include phenol, p-cumylphenol (PCP), p-tert-butylphenol, octylphenol, and p-cyanophenol. In particular embodiments, the endcapping agent is 4-hydroxybenzophenone (4-HBP). If desired, more than one monohydroxy compound can be used.

The carbonate precursor may be, for example, a carbonyl halide such as carbonyl dibromide or carbonyl dichloride (also known as phosgene), or a haloformate such as a bishaloformate of a dihydric phenol (e.g., the bischloroformate of bisphenol-A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In certain embodiments, the carbonate precursor is phosgene, a triphosgene, diacyl halide, dihaloformate, dicyanate, diester, diepoxy, diarylcarbonate, dianhydride, dicarboxylic acid, diacid chloride, or any combination thereof. An interfacial polymerization reaction to form carbonate linkages may use phosgene as a carbonate precursor, and is referred to as a phosgenation reaction.

The catalyst can be a tertiary amine or a phase transfer catalyst. Among tertiary amines that can be used are aliphatic tertiary amines such as triethylamine (TEA), N-ethylpiperidine, 1,4-diazabicyclo[2.2.2]octane (DABCO), tributylamine, cycloaliphatic amines such as N,N-diethylcyclohexylamine and aromatic tertiary amines such as N,N-dimethylaniline.

Among the phase transfer catalysts that can be used are catalysts of the formula $(R^{30})_4Q^+X$, wherein each $R^{30}$ is the same or different, and is a $C_1$-$C_{10}$ alkyl group; Q is a nitrogen or phosphorus atom; and X is a halogen atom, $C_1$-$C_8$ alkoxy group, or $C_6$-$C_{18}$ aryloxy group. Exemplary phase transfer catalysts include, for example, [CH₃(CH₂)₃]₄NX, [CH₃(CH₂)₃]₄PX, [CH₃(CH₂)₅]₄NX, [CH₃(CH₂)₆]₄NX, [CH₃(CH₂)₄]₄NX, CH₃[CH₃(CH₂)₃]₃NX, and CH₃[CH₃(CH₂)₂]₃NX, wherein X is Cl⁻, Br⁻, a $C_1$-$C_8$ alkoxy or $C_6$-$C_{18}$ aryloxy group, such as methyltributylammonium chloride.

The most commonly used water-immiscible solvents include methylene chloride, 1,2-dichloroethane, chlorobenzene, toluene, and the like.

If desired, a branching agent such as trishydroxyphenylethane (THPE) can be included.

In the first process, sometimes referred to as the "upfront" process, the diol(s), end-capping agent, catalyst, water, and water-immiscible solvent are combined upfront in a vessel to form a reaction mixture. The reaction mixture is then exposed to the carbonate precursor, for example by phosgenation, while the base is co-added to regulate the pH, to obtain the photoactive additive.

The pH of the reaction mixture is usually from about 8.5 to about 10, and can be maintained by using a basic solution (e.g. aqueous NaOH). The reaction mixture is then charged with the carbonate precursor, which is usually phosgene. The carbonate precursor is added to the reaction mixture over a period of about 15 minutes to about 45 minutes. While the carbonate precursor is being added, the pH is also maintained in the range of about 8.5 to about 10, again by addition of a basic solution as needed. The cross-linkable polycarbonate is thus obtained, and is then isolated from the reaction mixture.

In the second process, also known as the "solution addition" process, the diol(s), tertiary amine catalyst, water, and water-immiscible solvent are combined in a vessel to form a reaction mixture. The total charge of the carbonate precursor is then added to this reaction mixture in the vessel over a total time period, while the base is co-added to regulate the pH. The carbonate precursor is first added to the reaction mixture along with the base to regulate the pH for a first time period. After the first time period ends, the end-capping agent is added in a controlled manner to the reaction mixture, also referred to as programmed addition. The addition of the end-capping agent occurs for a second time period after the first time period, rather than as a bolus at the beginning of the reaction (as in the upfront process). The carbonate precursor and the base are also added concurrently with the end-capping agent during the second time period. After the second time period ends, the remainder of the carbonate precursor continues uninterrupted for a third time period until the total charge is reached. The base is also co-added during the third time period to regulate the reaction pH. The pH of the reaction mixture is usually from about 8.5 to about 10, and can be maintained by using a basic solution (e.g. aqueous NaOH, made from the base). The end-capping agent is not added during either the first time period or the third time period. The photoactive additive is thus obtained. The main difference between the first and second processes is in the addition of the end-capping agent over time.

In the second process, the carbonate precursor is added to the reaction mixture over a total time period, which may be for example from about 15 minutes to about 45 minutes. The total time period is the duration needed to add the total charge of the carbonate precursor (measured either by weight or by moles) to the reaction mixture. It is contemplated that the carbonate precursor is added at a constant rate over the total time period. The carbonate precursor is first added to the reaction mixture along with the base to regulate the pH for a first time period, ranging from about 2 minutes to about 20 minutes. Then, during a second time period, the end-capping agent is added to the reaction mixture concurrently with the carbonate precursor and the base. It is contemplated that the end-capping agent is added at a constant rate during this second time period, which can range from about 1 minute to about 5 minutes. After the second time period ends, the remaining carbonate precursor is charged to the reaction mixture for a third time period, along with the base to regulate the reaction pH. The cross-linkable polycarbonate is thus obtained, and is then isolated from the reaction mixture.

The total time period for the reaction is the sum of the first time period, the second time period, and the third time period. In particular embodiments, the second time period in which the solution containing the end-capping agent is added to the reaction mixture begins at a point between 10% to about 40% of the total time period. Put another way, the first time period is 10% of the total time period.

For example, if 2400 grams of phosgene were to be added to a reaction mixture at a rate of 80 g/min, and 500 ml of a PCP solution were to be added to the reaction mixture at a rate of 500 ml/min after an initial charge of 240 grams of phosgene, then the total time period would be 30 minutes, the first time period would be three minutes, the second time period would be one minute, and the third period would be 26 minutes.

The third process is also referred to as a bis-chloroformate or chlorofomate (BCF) process. Chloroformate oligomers are prepared by reacting the carbonate precursor, specifically phosgene, with the diol(s) in the absence of the tertiary amine catalyst, while the base is co-added to regulate the pH. The chloroformate oligomers can contain a mixture of monochloroformates, bischloroformates, and bisphenol terminated oligomers. After the chloroformate oligomers are generated, the phosgene can optionally be allowed to substantially condense or hydrolyze, then the end-capping agent is added to the chloroformate mixture. The reaction is allowed to proceed, and the tertiary amine catalyst is added to complete the reaction. The pH of the reaction mixture is usually from about 8.5 to about 10 prior to the addition of the phosgene. During the addition of the phosgene, the pH is maintained between about 6 and about 8, by using a basic solution (e.g. aqueous NaOH).

The fourth process uses a tubular reactor. In the tubular reactor, the end-capping agent is pre-reacted with the carbonate precursor (specifically phosgene) to form chloroformates. The water-immiscible solvent is used as a solvent in the tubular reactor. In a separate reactor, the diol(s), tertiary amine catalyst, water, and water-immiscible solvent are combined to form a reaction mixture. The chloroformates in the tubular reactor are then fed into the reactor over a first time period along with additional carbonate precursor to complete the reaction while the base is co-added to regulate the pH. During the addition of the chloroformates, the pH is maintained between about 8.5 and about 10, by using a basic solution (e.g. aqueous NaOH).

The crosslinkable polycarbonate is irradiated with ultraviolet light to cause crosslinking between polymeric chains. UV light has a wavelength between 10 nanometers and 400 nanometers (nm). The crosslinkable polycarbonate film is exposed to ultraviolet (UV) light at an appropriate wavelength and in an appropriate dosage to bring about a desired amount of crosslinking for the given application.

Where enhanced properties are needed, there should be enhanced exposure with a substantially uniform dose of UV light. The exposure can be accomplished using standard methods known in the art. For example, the UV light can come from any source of UV light such as, but not limited to, those lamps powered by microwave, HID lamps, and mercury vapor lamps. The exposure time will be dependent on the application and color of material. It can range from a few minutes to several days. Alternatively, the crosslinking can be accomplished by using a UV-emitting light source such as a mercury vapor, High-Intensity Discharge (HID), or various UV lamps. For example, commercial UV lamps are sold for UV curing from manufacturers such as Fusion UV. Non-limiting examples of UV-emitting light bulbs include H bulbs, D bulbs, H+ bulbs, and V bulbs. An H bulb has strong output in the range of 200 nm to 320 nm. The D bulb has strong output in the 320 nm to 400 nm range. The V bulb has strong output in the 400 nm to 420 nm range.

UV wavelengths can be separated into four different categories. UVA refers to wavelengths from 320 nm to 390 nm. UVB refers to wavelengths from 280 nm to 320 nm. UVC refers to wavelengths from 250 nm to 260 nm. UVV refers to wavelengths from 395 nm to 445 nm.

In particular embodiments, the polycarbonate fibers are exposed to a selected UV light range having wavelengths from about 280 nanometers (nm) to about 380 nm, or from about 330 nm to about 380 nm, or from about 280 nm to about 360 nm, or from about 330 nm to about 360 nm. The wavelengths in a "selected" light range have an internal transmittance of greater than 50%, with wavelengths outside of the range having an internal transmittance of less than 50%. The change in transmittance may occur over a range of 20 nm. Reference to a selected light range should not be construed as saying that all wavelengths within the range transmit at 100%, or that all wavelengths outside the range transmit at 0%.

In some embodiments, the UV radiation is filtered to provide exposure to UVA radiation with no detectable UVC radiation, as measured using an EIT PowerPuck. The effective dosage can range from at least 2 J/cm$^2$ of UVA radiation up to about 60 J/cm$^2$ of UVA radiation. In more specific embodiments, the UV radiation is filtered to provide an effective dosage of at least 3 J/cm$^2$, or at least 12 J/cm$^2$, or at least 21 J/cm$^2$, or at least 36 J/cm$^2$ of UVA radiation, with no detectable UVC radiation, as measured using an EIT PowerPuck. In particular embodiments, the polycarbonate fibers are exposed to a dosage of about 21 J/cm$^2$ to about 60 J/cm$^2$ of UVA radiation, or in more particular embodiments a dosage of about 21 J/cm$^2$ to about 36 J/cm$^2$ of UVA radiation.

Next, the storage modulus (G') versus temperature is determined for the crosslinked polycarbonate, and is measured as a function of UV exposure time as well. In this regard, the amount of crosslinking is known to be generally related to the UV exposure time, but this is insufficient to predict other properties. The storage modulus is generally derived from performing dynamic mechanical analysis (DMA) on the crosslinked polycarbonate. In Dynamic Mechanical Analysis (DMA), a sinusoidal force (stress) is applied to a solid state sample of the crosslinked polycarbonate (film or bar), and the resulting displacement (strain) is measured. DMA works by applying a sinusoidal deformation to a sample of known geometry. The sample can be subjected to a controlled stress or a controlled strain using a dynamic mechanical analyzer. For a known stress, the sample will then deform a certain amount. The amount of deformation is related to its stiffness. DMA is also called DMTA for Dynamic Mechanical Thermal Analysis. DMA may be calculated according to ASTM D5279.

In oscillatory rheology, a strain controlled rheometer is used to induce a sinusoidal shear deformation (i.e. the strain) in the sample when the sample is in a melt state, and the resultant stress response is measured. The time scale probed is determined by the frequency of oscillation of the shear deformation. Viscoelastic materials exhibit behavior between that of purely viscous and purely elastic materials, exhibiting some phase lag between stress and strain.

The storage modulus in viscoelastic solids measures the stored energy or elastic portion of viscoelastic materials. The storage modulus G' is defined in Eqn. 1:

$$G' = \frac{\text{Stress0}}{\text{Strain0}} \cos(\delta) \qquad \text{(Eqn. 1)}$$

where δ is the phase lag between the stress and strain in a viscoelastic polycarbonate.

When the storage modulus is plotted versus temperature for a polymer, certain features are clearly present on the graph. At low temperatures, the polymer is in a hard state, and has a high storage modulus. Once the glass temperature is reached, the polymer transitions to a molten or rubber-like state in which the storage modulus is lower. The storage modulus remains relatively constant, and this is referred to as the "rubber plateau." At even higher temperatures, the polymer melts, and the storage modulus drops even further. Put another way, the rubber plateau may be considered to be roughly bounded by the glass transition temperature (Tg) and the melting temperature (Tm).

It has been found that the amount of crosslinking, as measured by the gel thickness of the crosslinked polycarbonate, correlates with an average magnitude of the storage modulus G' over a specified temperature range in the rubber plateau. The range over which the average magnitude is determined is, in embodiments, at least 10°, or at least 20°, or at least 30°, or from about 10° to about 30°. For example, in certain specific embodiments, the average magnitude of the storage modulus is calculated over the temperature range of 160° C. to 190° C.; this is a 30° range. The storage modulus can be measured at regular intervals within the range, for example every 1° C. or every 5° C. or every 10° C.

In this regard, without being limited by theory, the size of the rubber plateau is indicative of an effectively crosslinked polycarbonate. The storage modulus measures the amount of energy stored by the crosslinking, and a need for higher temperatures to melt the polymer indicates that more crosslinking has occurred. Maintaining a high storage modulus over a wide temperature range is thus captured by the average magnitude of the storage modulus. This correlation has been confirmed by optical measurements of the gel thickness of several crosslinked polycarbonate films. The formation of gel indicates crosslinking, and the thickness relates to the amount of crosslinking that has occurred.

Generally speaking, it is believed that the amount of crosslinking that occurs can be affected by the UV dosage, the concentration of the photoactive moiety, and the type of UV light to which the polycarbonate is exposed.

Prediction of at least one of the flame retardance, chemical retardance, and mechanical properties of the crosslinked polycarbonate can performed by evaluating the crosslinked polycarbonate. These properties can be predicted by consulting a reference table correlating these properties to the average magnitude of the storage modulus size over the temperature range in the rubber plateau, or by comparing the average magnitude to a threshold value that indicates a particular property is likely to perform to specification.

Some flammability retardance tests may be defined according to the procedure of Underwriter's Laboratory Bulletin 94 entitled "Tests for Flammability of Plastic Materials, UL94." According to this procedure, materials may be classified as V-0, V-1, V-2, 5VA, or 5VB on the basis of the test results obtained for samples of a given thickness. It is assumed that a material that meets a given standard at a given thickness can also meet the same standard at greater thicknesses (e.g. a material that obtains V0 performance at 0.8 mm thickness can also obtain V0 performance at 1.0 mm thickness, 1.5 mm, etc.). The criteria for each of the flammability classifications tested are described below.

V0:

In a sample placed so that its long axis is 180 degrees to the flame, the average period of flaming and/or smoldering after removing the igniting flame does not exceed five seconds and none of the vertically placed samples produces drips of burning particles that ignite absorbent cotton, and no specimen burns up to the holding clamp after flame or after glow. Five bars flame out time (FOT) is the sum of the flame out time for five bars each lit twice for ten (10) seconds each, for a maximum flame out time of 50 seconds. FOT1 is the average flame out time after the first light. FOT2 is the average flame out time after the second light.

V-1, V-2:

In a sample placed so that its long axis is 180 degrees to the flame, the average period of flaming and/or smoldering after removing the igniting flame does not exceed twenty-five seconds and, for a V-1 rating, none of the vertically placed samples produces drips of burning particles that ignite absorbent cotton. The V2 standard is the same as V-1, except that flaming drips that ignite the cotton are permitted. Five bar flame out time (FOT) is the sum of the flame out time for five bars, each lit twice for ten (10) seconds each, for a maximum flame out time of 250 seconds.

5VB:

a flame is applied to a vertically fastened, 5-inch (127 mm) by 0.5-inch (12.7 mm) test bar of a given thickness above a dry, absorbent cotton pad located 12 inches (305 mm) below the bar. The thickness of the test bar is determined by calipers with 0.1 mm accuracy. The flame is a 5-inch (127 mm) flame with an inner blue cone of 1.58 inches (40 mm). The flame is applied to the test bar for 5 seconds so that the tip of the blue cone touches the lower corner of the specimen. The flame is then removed for 5 seconds. Application and removal of the flame is repeated for until the specimen has had five applications of the same flame. After the fifth application of the flame is removed, a timer (T-0) is started and the time that the specimen continues to flame (after-flame time), as well as any time the specimen continues to glow after the after-flame goes out (after-glow time), is measured by stopping T-0 when the after-flame stops, unless there is an after-glow and then T-0 is stopped when the after-glow stops. The combined after-flame and after-glow time must be less than or equal to 60 seconds after five applications of a flame to a test bar, and there may be no drips that ignite the cotton pad. The test is repeated on 5 identical bar specimens. If there is a single specimen of the five does not comply with the time and/or no-drip requirements then a second set of 5 specimens are tested in the same fashion. All of the specimens in the second set of 5 specimens must comply with the requirements in order for material in the given thickness to achieve the 5VB standard.

5VA:

In addition to meeting the 5VB standard, a set of three plaques having the same thickness as the bars are tested in a horizontal position with the same flame. No test plaque specimen can exhibit a burn-through hole.

In the present disclosure, as a proxy for 5VA performance, the specimens are exposed to the flame until a hole is formed, and this time is referred to as Time To Hole (TTH). Generally, a TTH value above 70 seconds indicates that the specimen is likely to achieve UL94 5VA performance. However, it is noted that this TTH test is a proxy, and is not itself compliant with UL94.

The following examples are provided to illustrate the methods of the present disclosure. The examples are merely illustrative and are not intended to limit the disclosure to the materials, conditions, or parameters set forth therein.

EXAMPLES

Samples were sometimes exposed to various doses of either filtered or unfiltered UV light. The unfiltered light was provided by a Fusion UV conveyor system, which used a D-bulb electrodeless bulb. The filtered light was provided by a Loctite Zeta 7411-S system, which used a 400 W metal halide arc lamp and behaved like a D-bulb electrodeless bulb in spectral output with a 280-nm cut-on wavelength filter. The UV energy (for given exposure time, or per pass) for each system is provided below in Table A and Table B, and was measured using an EIT PowerPuck. The dose was measured as the energy from 320-390 nm (UVA)), 280-320 nm (UVB), 250-260 nm (UVC) and 395-445 nm (UVV). The dose was calculated in $J/cm^2$.

TABLE A

| Loctite (filtered light). | | | | |
|---|---|---|---|---|
| Loctite Dose Filtered | UVA $J/cm^2$ | UVB $J/cm^2$ | UVC $J/cm^2$ | UVV $J/cm^2$ |
| 160 sec | 6 | | | |
| 320 sec | 12 | 2.4 | 0 | 7.3 |
| 480 sec | 18 | | | |
| 640 sec | 24 | | | |
| 800 sec | 30 | | | |
| 960 sec | 36 | 7.2 | 0 | 21.9 |

TABLE B

| Fusion (unfiltered light) | | | | |
|---|---|---|---|---|
| Fusion UV Unfiltered | UVA $J/cm^2$ | UVB $J/cm^2$ | UVC $J/cm^2$ | UVV $J/cm^2$ |
| 1 pass | 6 | | | |
| 2 passes | 12 | 3.7 | 0.45 | 5.8 |
| 3 passes | 18 | | | |
| 4 passes | 24 | | | |
| 5 passes | 30 | | | |
| 6 passes | 36 | 11.0 | 1.34 | 17.5 |
| 7 passes | 42 | | | |
| 15 passes | 90 | | | |
| 20 passes | 120 | | | |
| 25 passes | 150 | | | |

Example 1

The term "LF-XPC" refers to a low flow crosslinkable polycarbonate resin of bisphenol-A having 3.5 mole % of 4-hydroxybenzophenone (4-HBP) endcapping agent. The LF-XPC has a weight average molecular weight (Mw) of about 31,0000.

The LF-XPC was blended with 0.1 phr of octaphenylcyclotetrasiloxane, 0.08 phr Rimar salt, and 0.06 phr phosphite stabilizer (tris(2,4-di-tert-butylphenyl)phosphite). Plaques were made from this blend and were irradiated by passing them under a UV lamp using a conveyor having a constant travel rate. Plaques were removed after 2, 5, or 10 passes, the number of passes serving as a proxy for the amount of UV exposure.

Small amplitude oscillatory shear rheology measurements were run on the different plaques, including a control plaque with zero exposure to UV light, at 300° C. The dynamic oscillatory frequency sweeps were run using an ARES strain controlled rheometer. The frequency sweep method was used to determine the viscosity or modulus of a material as a function of frequency at a constant temperature (300° C.). The measurements were performed using 25 mm parallel-plate geometry at a 20% strain (linear regime) with a fixed gap of 1 mm. The frequency was varied from 0.1 to 500 rad/s.

FIG. 1 shows the results, measuring the storage modulus G' as a function of the frequency and the number of UV passes on the Fusion system. Each pass was roughly equivalent to a dosage of 6-7 $J/cm^2$ of UVA energy. As the number of passes increased, the storage modulus increased at each frequency. The increase in storage modulus was up to several orders of magnitude, depending on the frequency. as a function of UV exposure time. This increase in modulus indicated increased cross-linking in the LF XPC resins.

Solid State Rheology and Gel Analysis on the LF XPC Films.

Next, LF-XPC plaques were irradiated from 3 to 40 passes using different UV bulbs on one side with the intent to be analyzed using a Dynamic Mechanical Analyzer (DMA) (Q800, TA Instruments). The DMA is a precision instrument designed to measure viscoelastic properties as a function of temperature. All the measurements performed on the DMA were run in a tensile mode with a frequency of 1 Hz, at a strain level of 0.01%, in the temperature range from 30° C. to 200° C. The heating rate was 3° C./min. The testing was performed using rectangular plaques having thickness of about 1 mm or 1.2 mm.

The storage modulus, G' (MPa) versus temperature was recorded as a function of UV passes for a film/plaque having a thickness of 1 millimeter (mm). Those results were compared with gel thickness. To obtain the gel thickness, samples (bars or films) were received in a 2 ounce flint bottle as a molded part, placed in $CH_2Cl_2$, and shaken overnight. Typically, what appeared to be the skin of one surface of the part remained after this treatment. The skin was removed by tweezers and placed onto heavy gauge aluminum foil. A mid-section of approximately one-quarter inch to one-half inch (cut using a clean sharp razor blade) was placed into an aluminum pan with sufficient $CH_2Cl_2$ to cover the section, and the remainder was returned to the bottle. It was noted that the section generally immediately rolled up when removed from the $CH_2Cl_2$.

If the section had a thickness greater than 10 or 15 microns, the section was manipulated with micro-tools into a configuration of a double rolled section (resembling a scroll). The rolled section was then lifted from the $CH_2Cl_2$ by inserting a tapered micro-tool into one roll and placed onto clean aluminum foil. With a second micro-tool in the other roll of the "scroll," the micro-tools were slowly pulled apart, rolling the section out flat onto the foil. The foil could then be folded onto the section to hold the section in place. Residual $CH_2Cl_2$ was permitted to flash evaporate. An applied temperature of about 60° C.-80° C. could speed this process.

If the section was thinner than 10 microns, the skin was not lifted out of the $CH_2Cl_2$. Instead, to prevent damage to the section, most of the $CH_2Cl_2$ was flash evaporated while separating the edges of the section with micro-tools. The section was slowly expanded until flat. The remaining $CH_2Cl_2$ was then flash evaporated. Again, an applied temperature of about 60° C.-80° C. could speed this process.

Once the $CH_2Cl_2$ was removed, the section of the skin could be cut into a narrow (about 500 micron) strip with parallel sides using a clean sharp razor blade. The strip was mounted edgewise onto double-sided carbon or copper SEM tape. Intermediate images (informational, 8.1×-101× magnification) were captured via Zeiss Discovery imaging microscope and software. Final images (cross section thicknesses, 25×-1000× magnification) were captured via Zeiss Axioplan imaging microscope and software. Different locations were selected so as to acquire representative measurements. These results are presented in Table 1.

TABLE 1

| UV Bulb Type | # of Passes Under UV | Gel Thickness (μm) |
|---|---|---|
| UV-D | 3 | N/A |
| UV-D | 40 | 25.62 |
| UV-D | 30 | 17.97 |
| UV-H | 5 | 1.16 |
| UV-H | 10 | 1.24 |
| UV-H | 20 | 3.20 |
| UV-H | 30 | 5.82 |
| UV-V | 3 | No Gel |
| UV-V | 30 | No Gel |

Figure 2:
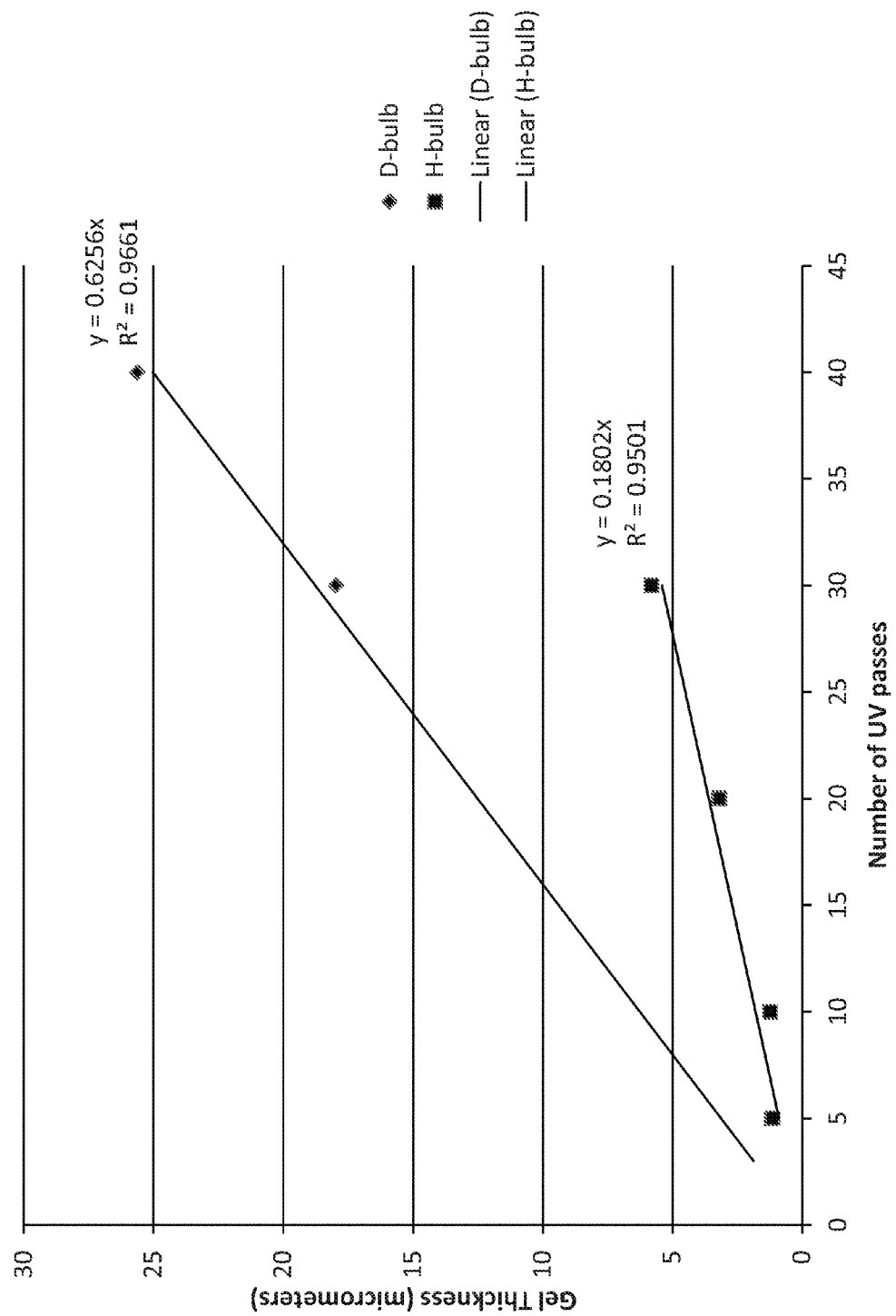
FIG. 2 is a graph showing the gel thickness versus number of UV passes for two different UV bulb types. The bulb type affects the gel thickness.

As previously mentioned, an H bulb has a strong output in the range of 200 nm to 320 nm. The D bulb has a strong output in the 320 nm to 400 nm range. The V bulb has a strong output in the 400 nm to 420 nm range. Based on the gel thickness measurements, there is a correlation between the bulb type and the resulting gel thickness, as shown in FIG. 2. The D bulb produced a greater gel thickness for a given number of passes. A V bulb did not result in cross-linking at all, suggesting that wavelengths higher than 400 nm did not activate the 4-HBP.

Figure 3:
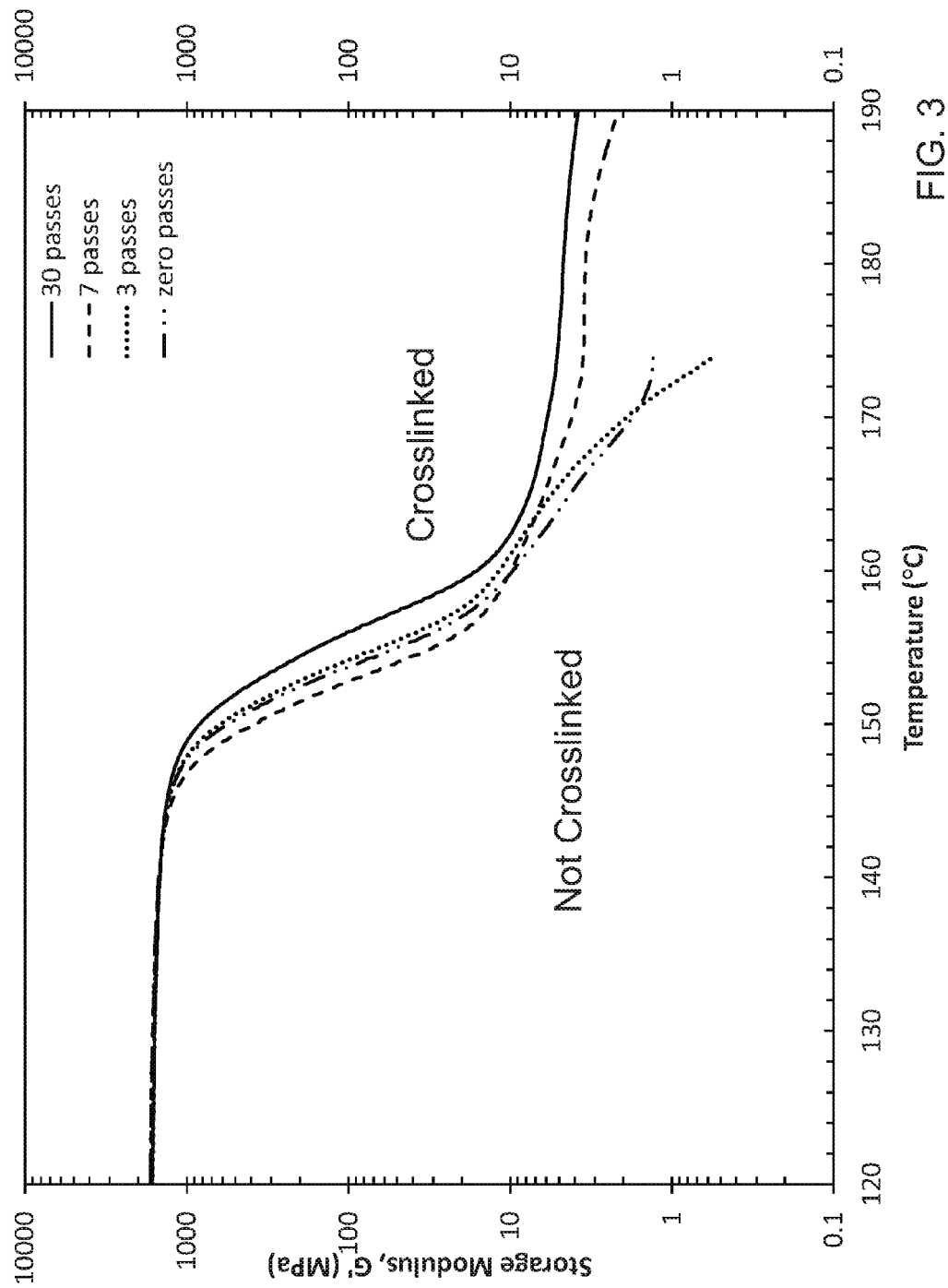
FIG. 3 is a graph showing the measured storage modulus versus temperature as a function of the number of UV passes (proxy for UV exposure time). The 30-pass line is the top line at the far right, and the 7-pass line is the second from the top at the far right. The 3-pass line is the lowest line on the far right. The zero-pass line is the second lowest line on the far right.

FIG. 3 is a graph showing the storage modulus versus temperature for films having a different number of UV passes (0, 3, 7, and 30). At any given temperature, e.g., 175° C., the storage modulus increased from 0.3 MPa at 3 passes to 5 MPa at 30 passes. Upon noting that the curves are different in the rubber plateau but have some overlapping values at given temperatures, the average magnitude over a 30° C. temperature range was used instead. This average storage modulus in the rubber plateau was found to correlate to the increase in gel thickness.

In FIG. 3, both 7 and 30 UV passes showed a relatively level storage modulus plateau, which is indicative of cross-linking. By contrast, zero passes and 3 passes generally continued their downward slope and had a very small (if any) plateau, indicating a lack of crosslinking.

Next, three different blends were made with the LF-XPC described above (containing 3.5 mole % of 4-HBP). The LF-XPC was blended with either a low-flow bisphenol-A homopolymer (LF-BPA) or a high-flow bisphenol-A homopolymer (HF-BPA). The low-flow bisphenol-A homopolymer had an Mw of about 29,367 and an MFI of 6.4 g/10 min. The high-flow bisphenol-A homopolymer had an Mw of about 22,500 and an MFI of about 25 g/10 min. A cyclic siloxane (octaphenylcyclotetrasiloxane) was added, along with Rimar salt (flame retardant) and a phosphite stabilizer (tris(2,4-di-tert-butylphenyl)phosphite). Three controls were also used. The compositions and amounts of each ingredient are listed in Table 2, as well as some measured properties of the blends. It is noted that a lower melt flow index (MFI) means a higher weight average molecular weight.

Figure 4:
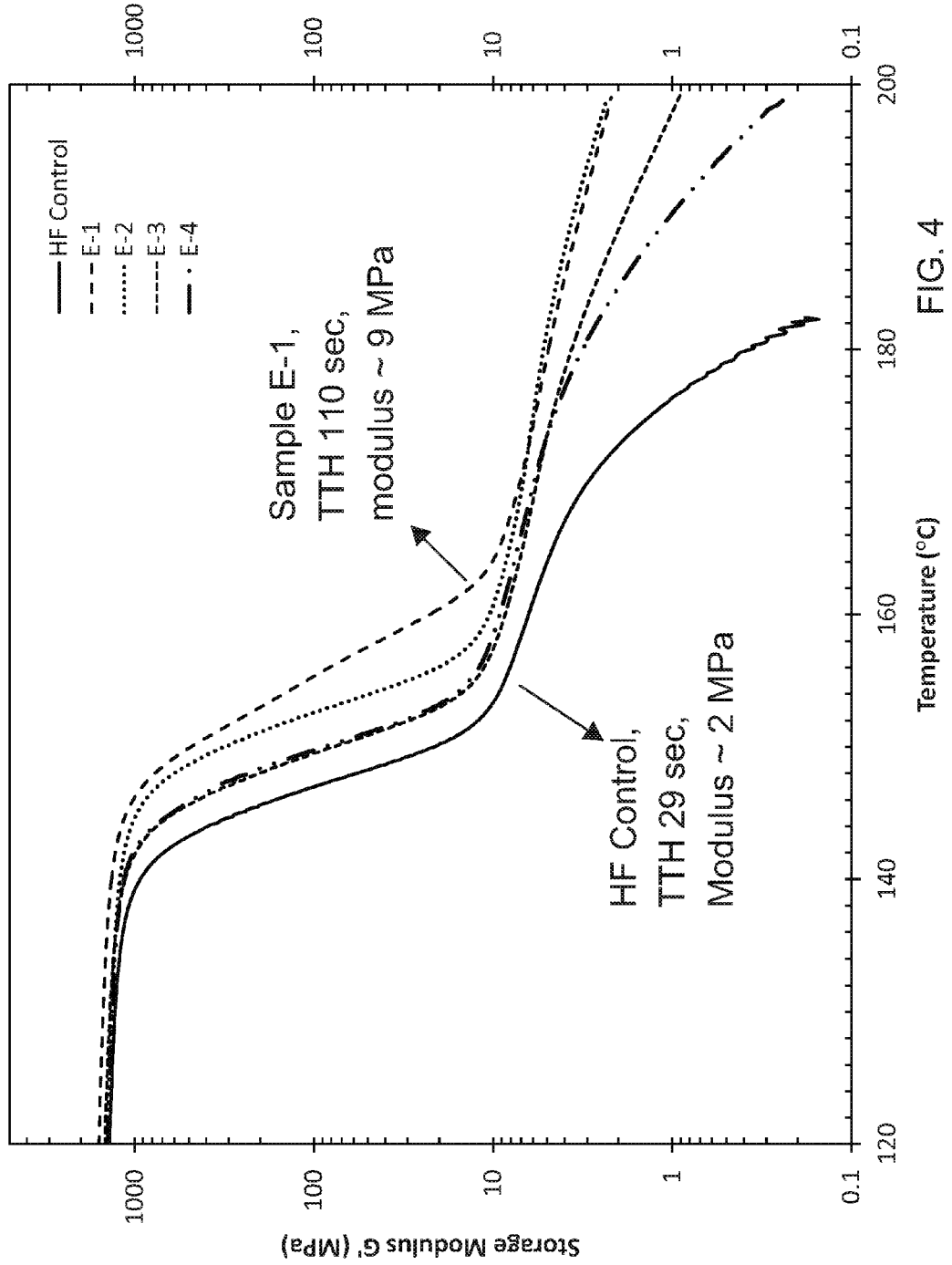
FIG. 4 is a graph showing the measured storage modulus versus temperature for a series of polycarbonate films containing different amounts of 4-hydroxybenzophenone (4-HBP) endcap. The control is the solid line, and ends at approximately 182.5° C. Line E-4 ends at the far right at magnitude of 0.2 MPa. Line E-3 ends at the far right at magnitude about 0.8 MPa. Line E-2 ends at the far right at about magnitude 3.0 MPa. Line E-1 also ends on the far right at about magnitude 3.0 MPa.

DMA measurements were made on thin flame bars (1.2 mm) made from the five compositions listed above and exposed to UV exposure for 5 passes (30 J/cm$^2$) on both sides in the Fusion system, with different amounts of 4-HBP endcapping agent. The bars were also measured for 5VA performance. FIG. 4 is a graph showing the storage modulus vs. temperature, and Table 3 contains the 5VA data and the average modulus.

TABLE 3

| Sample Number | 4-HBP % | Time To Hole [TTH] (sec) | Avg Modulus (MPa) |
|---|---|---|---|
| E-1 | 3.5 | >100 | ~9 |
| E-2 | 1.75 | 70 | ~7 |
| E-3 | 1.75 | 63 | ~5 |
| E-4 | 0.875 | 43.3 | ~4 |
| HF Control | 0 | 29 | ~2 |
| LF Control | 0 | 41 | ~4 |

Initially, referring to Table 2, the TTH was proportional to the amount of 4-HBP. Referring to FIG. 4, the average modulus was calculated over a temperature range of 160° C. to 190° C. For the sample E-1, having the highest amount of 4-HBP and a TTH of >100 seconds, the average modulus was about 9 MPa. In contrast, for the HF control having zero 4-HBP and a TTH of 29 seconds, the average modulus was about 2 MPa. The rubber plateau for the control was very small. The difference between E-2 and E-3 is likely due to the bisphenol-A homopolymer in the blend and the difference in MFI. The LF Control sample with zero 4-HBP demonstrated a poor TTH performance compared to the samples containing 4-HBP. Also, it was interesting to note that the molecular weights of the samples having 4-HBP were much lower than than the LF Control. The presence of 4-HBP clearly affected the rubber plateau of the polycarbonate, demonstrating the crosslinking ability of the 4-HBP and its effect on flame retardance. Based on FIG. 4, if the average modulus is greater than or equal to 9 MPa, then the sample is likely to pass the UL94 5VA standard. Put another way, 9 MPa could be considered a threshold value for passing the UL94 5VA test. The factors affecting the average modulus were the weight average molecular weight and the amount of crosslinking.

Figure 5:
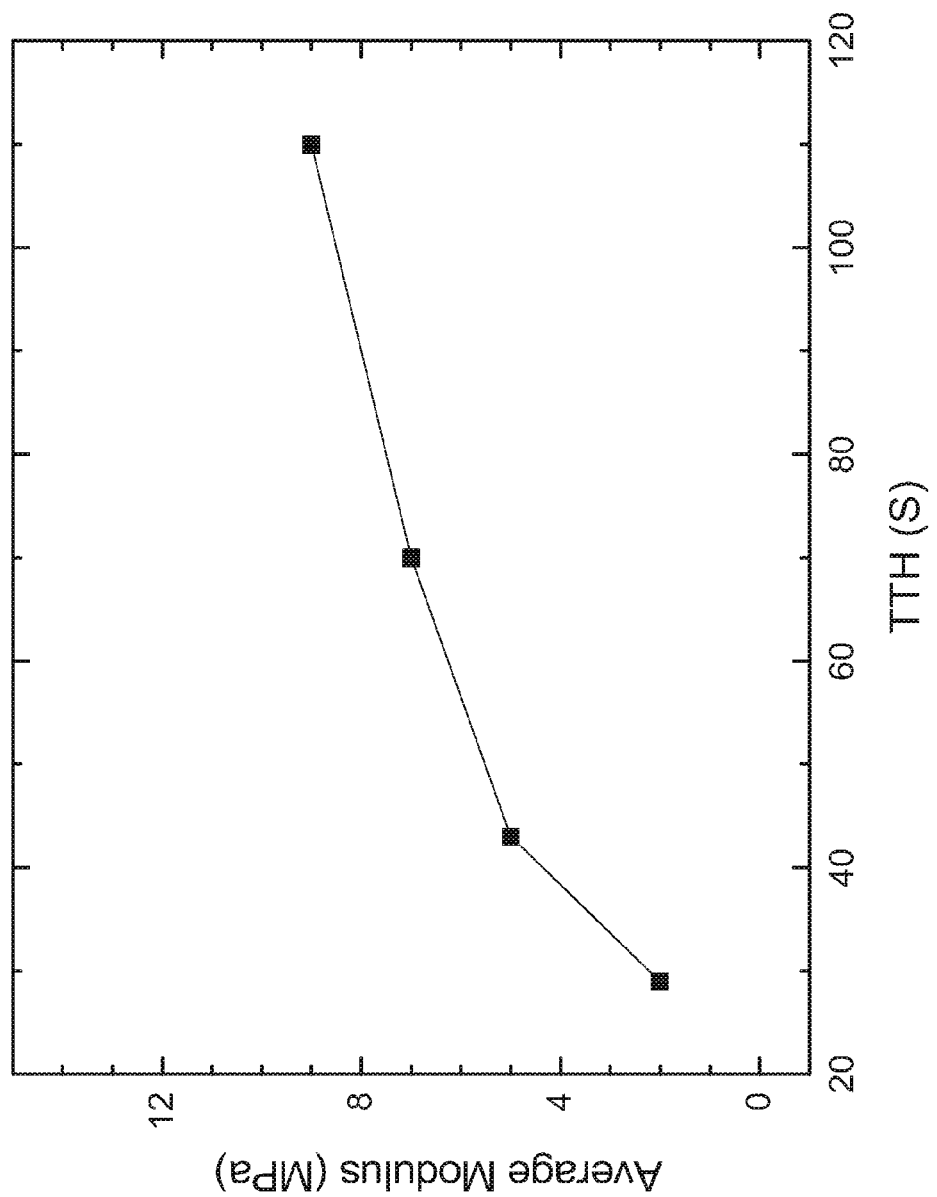
FIG. 5 is a graph showing the average modulus versus the Time To Hold (TTH) in seconds, a proxy for flame performance, for the samples of FIG. 4 containing different amounts of 4-HBP endcap.

FIG. 5 is a graph showing the average modulus versus the TTH. This graph shows that the two are roughly proportional to each other.

Next, additional samples were prepared by blending the LF-XPC (3.5 mol % 4HBP) with the HF-BPA or the LF-BPA described above to achieve the HBP levels listed in Table 4. Each sample also contained 0.1 phr of octaphenylcyclotetrasiloxane, 0.08 phr Rimar salt, and 0.06 phr phosphite stabilizer (tris(2,4-ditert-butylphenyl)phosphite). The

TABLE 2

Figure 6:
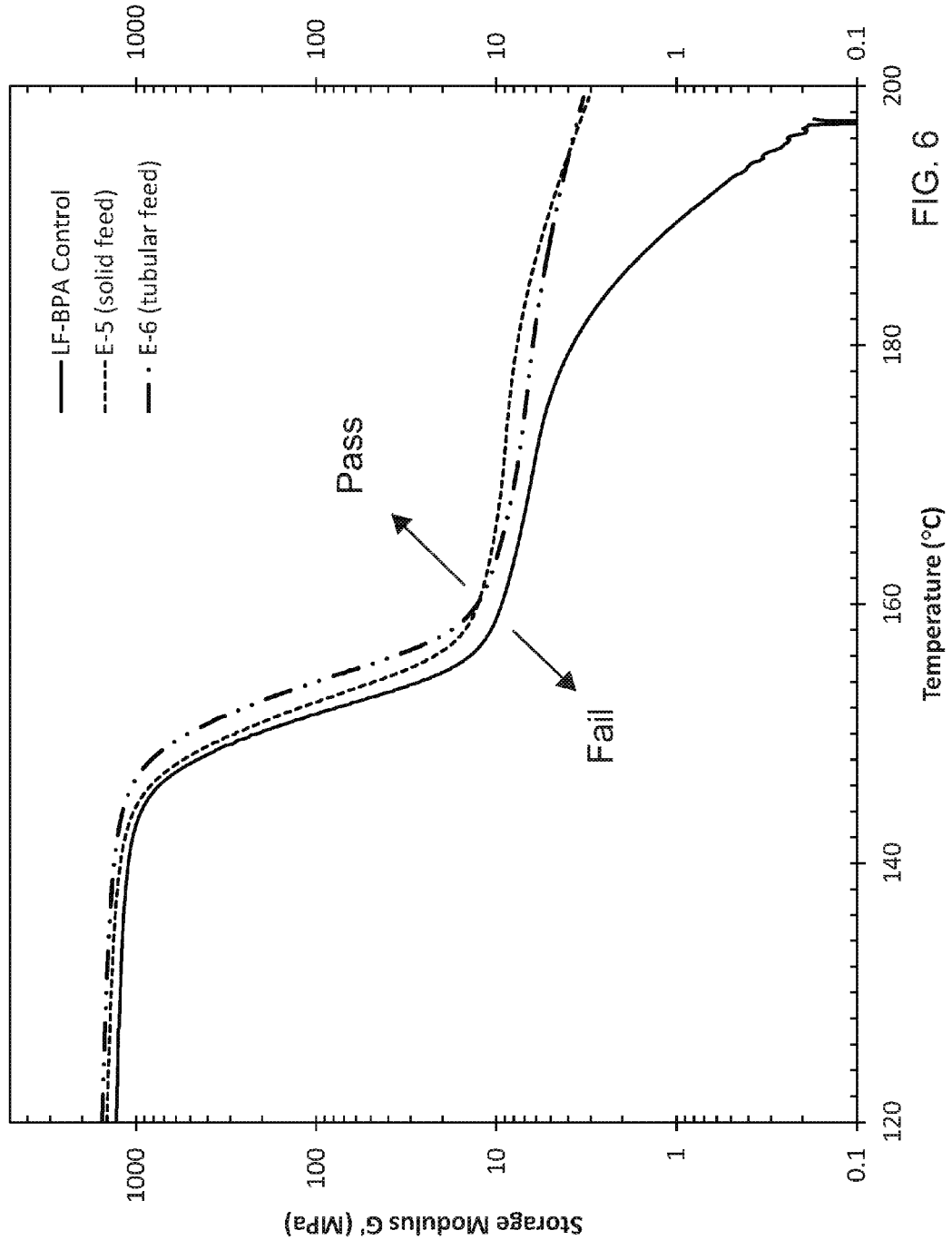
FIG. 6 is a graph showing the measured storage modulus versus temperature for a control bisphenol-A homopolycarbonate containing zero 4-HBP and two bisphenol-A polycarbonates containing 1.75 mole % of 4-HBP, but made using two different processes. The control is the bottom line (solid), the "solid feed" process is in dashes, and the "tube" process is the dash-dot-dot line.

| Sample | E-1 | E-2 | E-3 | E-4 | HF Control | LF Control |
|---|---|---|---|---|---|---|
| LF-XPC | 100 | 50 | 50 | 25 | | |
| LF-BPA | | 50 | | | | 100 |
| HF-BPA | | | 50 | 75 | 100 | |
| Cyclic siloxane (phr) | 0.10 | 0.10 | 0.10 | 0.10 | 0.10 | 0.10 |
| Rimar salt (phr) | 0.08 | 0.08 | 0.08 | 0.08 | 0.08 | 0.08 |
| Phosphite stabilizer (phr) | 0.06 | 0.06 | 0.06 | 0.06 | 0.06 | 0.06 |
| Total % HBP | 3.5 | 1.75 | 1.75 | 0.875 | 0 | 0 |
| MFI (g/10 min) | 9.8 | 7.3 | 16.5 | 22.2 | 31.1 | 6.4 |
| Mw | 21,678 | 24,699 | 21,431 | 20,656 | 20,301 | 29,367 | samples generally varied in the process by which they were made. The control was the LF-BPA, which is a bisphenol-A homopolymer containing no 4-HBP and made using the caustic cofeed process (all reactants mixed together, the pH controlled during phosgenation). DMA measurements were repeated on thin flame bars (1.2 mm) exposed to UV exposure for 5 passes (30 J/cm$^2$) on both sides in the Fusion system. These were also tested for various properties. FIG. 6 and Table 4 provide the results.

TABLE 4

| Sample No. | Blended With | Process | XPC Level | MFI | V0 Rating 1.2 mm | Mw | Avg Modulus 160° C.-190° C. |
|---|---|---|---|---|---|---|---|
| LF-BPA | — | Caustic Cofeed | 0 | 6.4 | Fail | 29,367 | ~2 |
| E-5 | LF-BPA | Upfront Solid Feed | 1.75 | 7.6 | Pass | 24,260 | ~9 |
| E-6 | LF-BPA | Tubular | 1.75 | 4.7 | Pass | 27,673 | ~9 |
| E-7 | HF-BPA | Caustic Cofeed | 1.75 | 8.5 | Fail | 24,537 | ~7 |
| E-8 | LF-BPA | Caustic Cofeed | 1.75 | 7.3 | Pass | 24,699 | ~9 |
| E-9 | HF-BPA | Caustic Cofeed | 1.75 | 16.5 | Fail | 21,431 | ~4 |
| E-10 | LF-BPA | BCF | 1.75 | 8.3 | Pass | 24,545 | ~9 |
| E-11 | — | Caustic Cofeed | 3.5 | 9.8 | Pass | 31,000 | ~9 |
| E-12 | LF-BPA | BCF | 1.75 | 16 | Fail | 21,600 | ~4 |

The MFI is the melt flow index, is reported in g/10 min, and was measured using ISO 1133 or ASTM D1238 at 300° C. and a 1.2 kg load. The Mw is the weight average molecular weight, and was measured by GPC using polycarbonate standards.

As seen in FIG. 6, the presence of 4-HBP clearly affected the rubber plateau of the polycarbonate, demonstrating the crosslinking ability of the 4-HBP, regardless of the manufacturing process. As indicated in Table 3, the crosslinked polycarbonates had improved flame retardance.

Figure 7:
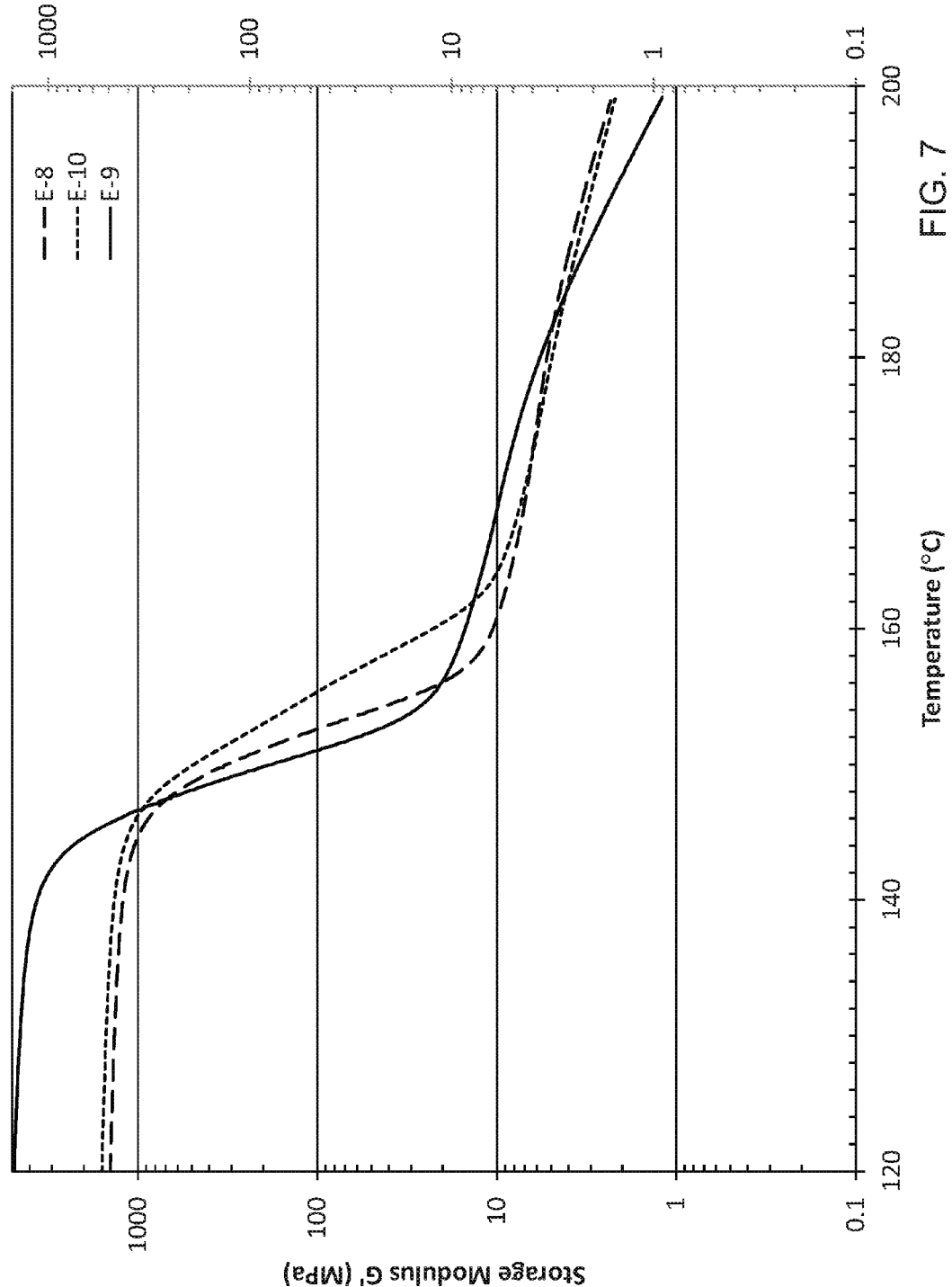
FIG. 7 is a graph showing the measured storage modulus versus temperature for several samples made using different processes.

As seen in FIG. 7, the average modulus generally correlated with the pass/fail, and the manufacturing process did not change this correlation.

Crosslinking Depth Analysis.

To understand the magnitude of crosslinking versus depth, a set of seven (7) films (each 200 microns thick) were clamped together on a glass slide and irradiated for 10 passes (dosage-60 J/cm$^2$) from the top layer to bottom.

Figure 8:
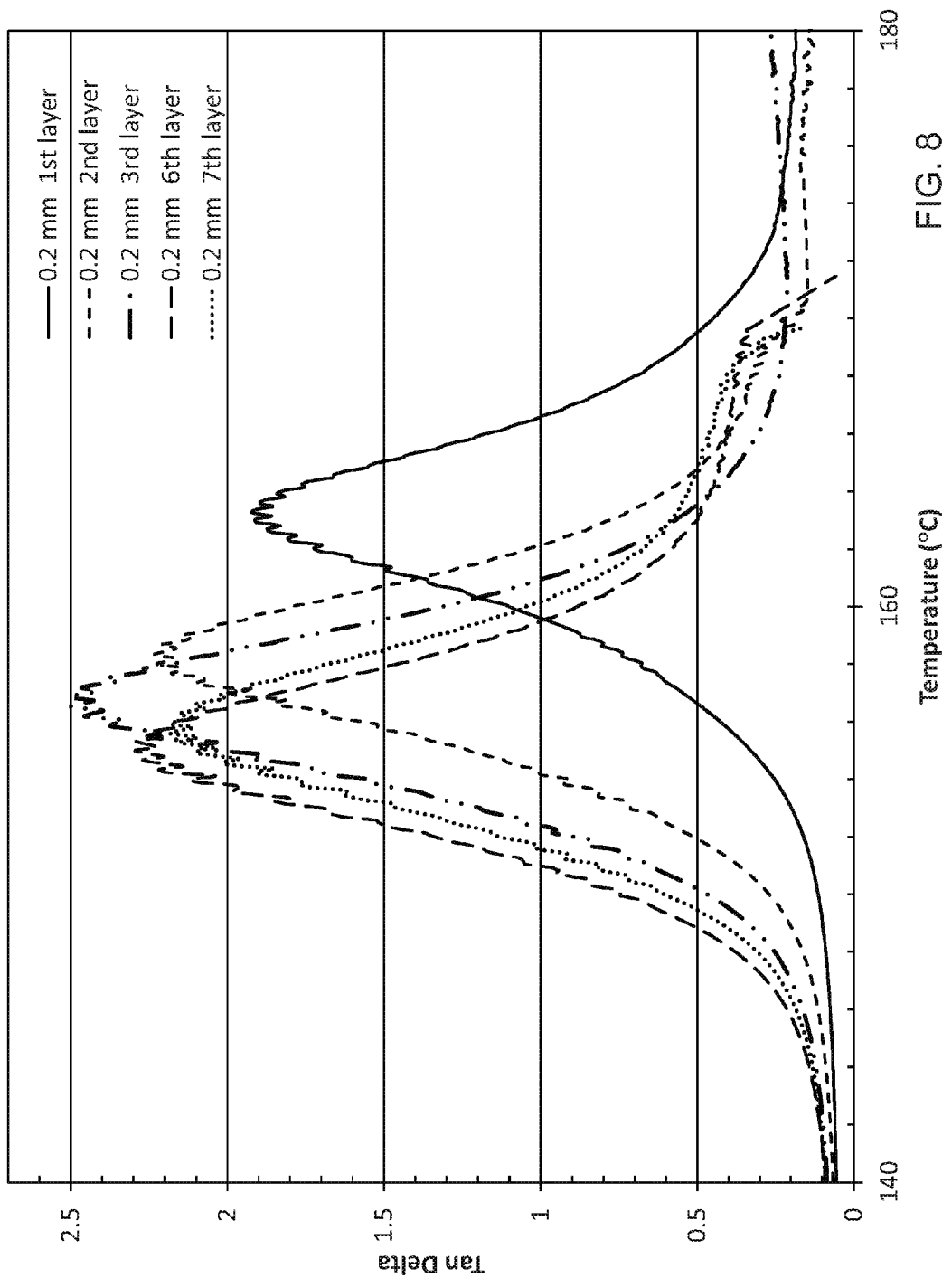
FIG. 8 is a graph showing the tan delta versus temperature for a set of seven films stacked upon each other and irradiated, and is used to measure the depth to which crosslinking occurs.
Figure 9:
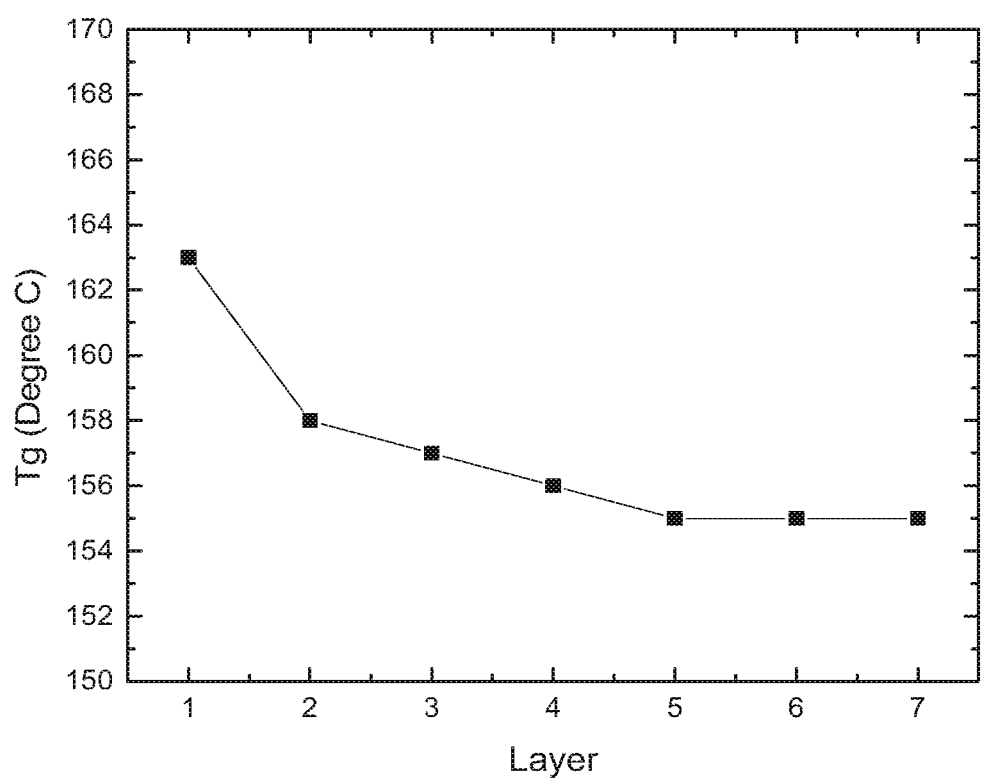
FIG. 9 is a graph showing the Tg versus the layer. This indicates to what depth crosslinking occurred.

FIG. 8 is a graph showing the tan delta versus temperature for each layer. The first layer was the layer on top, directly irradiated, while the seventh layer was the deepest layer (after the light passed through the other six layers). The tan delta is the ratio of the storage modulus to the loss modulus, and the peak of the tan delta indicates the glass transition temperature (Tg), which is plotted by itself in FIG. 9.

A significant difference (7° C.) in the $T_g$ between the first layer and the seventh layer was observed. This indicates that the first layer is highly cross-linked. Crosslinking occurs in layers 1-4, as indicated by the glass transition temperature (Tg). There is very little crosslinking in layers 5-7 (i.e. no change in Tg).

Example 2

The term "XPC-DHBP" refers to a crosslinkable copolycarbonate resin of bisphenol-A and 10 mole % 4,4'-dihydroxybenzophenone (4,4'-DHBP), which has a Mw of about 21,000.

Figure 10:
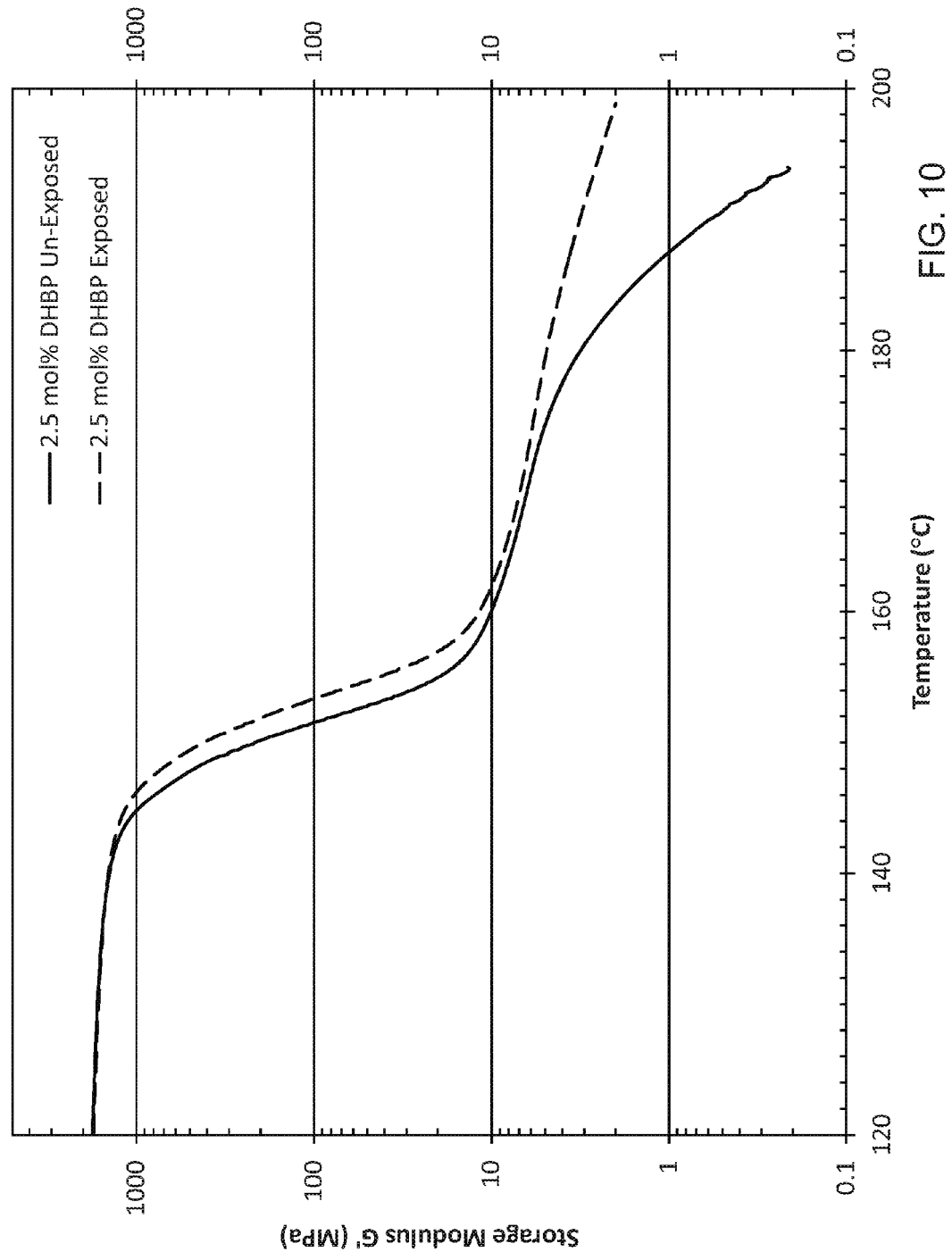
FIG. 10 is a graph showing the measured storage modulus versus temperature for a blend containing 2.5 mol % of 4,4'-dihydroxybenzophenone, both before and after UV exposure.

25 parts XPC-DHBP was blended with 75 parts LF-BPA, 0.08 parts Rimar salt, and 0.06 parts phosphite stabilizer, to arrive at a blend containing 2.5 mol % of 4,4'-DHBP. Plaques were made from the blend. One plaque was exposed to a UV dosage of 36 J/cm$^2$ on the Loctite system, while one was not exposed to UV at all. Dynamic mechanical analysis was then performed. FIG. 10 is a graph showing the storage modulus versus temperature. The exposed plaque is the dashed line, while the control un-exposed plaque is the solid line.

The exposed sample showed a relatively strong rubbery plateau (above Tg), which is a indicative of strongly crosslinked network. It also showed a very significant mechanical integrity above Tg. For example, at 190° C., the storage modulus value of the exposed sample was about 3.1 MPa, whereas the un-exposed sample had a value of only 0.5 MPa.

In later flame performance testing, the exposed sample passed the UL 5 VA test, while the un-exposed sample did not pass. This difference was predicted due to the difference in the storage modulus.

The disclosure is further illustrated by the following embodiments.

In an embodiment, a method for determining the flame performance of a crosslinked polycarbonate, preferably wherein the crosslinked polycarbonate is a bisphenol-A homopolymer having endcaps derived from 4-hydroxybenzophenone, a bisphenol-A copolymer having co-monomers derived from 4,4'-dihydroxybenzophenone, or a combination thereof, wherein the method comprises: measuring the storage modulus (G') versus temperature of the crosslinked polycarbonate using dynamic mechanical analysis, the measurement including a rubber plateau of the polycarbonate, preferably wherein the temperature range over which the average magnitude is determined is at least 10° C., preferably at least 30° C.; extrapolating an average magnitude of the storage modulus over a temperature range within the rubber plateau, preferably wherein the average storage modulus is determined by averaging between 160° C. and 190° C.; and determining the flame performance of the crosslinked polycarbonate based on the average magnitude of the storage modulus, preferably wherein the flame performance is determined by comparing the average magnitude of the storage modulus to a reference table, a threshold value or both.

In another embodiment, a method for selecting a crosslinkable polycarbonate that will achieve UL94 5VA performance at a thickness of 1.5 mm comprises: molding a part from a composition comprising a crosslinkable polycarbonate resin that contains an aromatic ketone-containing moiety derived from a dihydroxy compound or a monohydroxy compound, a bisphenol-A homopolymer having endcaps derived from 4-hydroxybenzophenone, a bisphenol-A copolymer having co-monomers derived from 4,4'-dihydroxybenzophenone, or a combination thereof, and a flame retardant additive; exposing the molded part to ultraviolet light to induce crosslinking; measuring the storage modulus (G') versus temperature of the molded part using dynamic mechanical analysis, the measurement including a rubber plateau of the polycarbonate, preferably wherein the temperature range over which the average magnitude is determined is at least 10° C., preferably at least 30° C.; extrapolating an average magnitude of the storage modulus over a temperature range within the rubber plateau, preferably wherein the average storage modulus is determined by averaging between 160° C. and 190° C.; and selecting the polycarbonate resin if the G' is 5 or greater.

Another embodiment is a polycarbonate composition, and an article comprising the polycarbonate composition, wherein the polycarbonate composition comprises a flame retardant additive; and at least one crosslinkable polycarbonate resin that contains an aromatic ketone-containing moiety derived from a dihydroxy compound or a monohydroxy compound, preferably a bisphenol-A homopolymer having endcaps derived from 4-hydroxybenzophenone, a bisphenol-A copolymer having co-monomers derived from 4,4'-dihydroxybenzophenone, or a combination thereof, and preferably further comprising a non-crosslinkable polycarbonate resin; wherein an article which is molded from the polycarbonate composition and exposed to ultraviolet light will have an average storage modulus of 5 or greater when averaged over a temperature range of at least 10° C., preferably at least 30° C. within the rubber plateau, more preferably wherein the average storage modulus is determined by averaging between 160° C. and 190° C.; and preferably wherein the composition has one, two, or most preferably all three of the following properties: an MFI of 4 to 10 g/10 min as measured at 300° C., 1.2 kg; the molded article achieves UL94 5VA performance at a thickness of 1.5 mm, and the molded article achieves UL94 V0 performance at a thickness of 1.2 mm.

In still another embodiment, a method for selecting a crosslinkable polycarbonate that will achieve UL94 V0 performance at a thickness of 1.2 mm, comprises: molding a part from a composition comprising a crosslinkable polycarbonate resin that contains an aromatic ketone-containing moiety derived from a dihydroxy compound or a monohydroxy compound, and a flame retardant additive; exposing the molded part to ultraviolet light to induce crosslinking; measuring the storage modulus (G') versus temperature of the molded part using dynamic mechanical analysis, the measurement including a rubber plateau of the polycarbonate, preferably wherein the temperature range over which the average magnitude is determined is 10° C., preferably 30° C., or wherein the average storage modulus is determined by averaging between 160° C. and 190° C.; extrapolating an average magnitude of the storage modulus over a temperature range within the rubber plateau; and selecting the polycarbonate resin if the G' is 9 or greater.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method for determining the flame performance of a composition comprising a crosslinked polycarbonate and a fixed amount of a flame retardant and a fixed amount of a cyclic siloxane, comprising:
measuring the storage modulus (G') versus temperature of the composition using dynamic mechanical analysis, the measurement including a rubber plateau of the composition;
extrapolating an average magnitude of the storage modulus over a temperature range within the rubber plateau; and
determining the flame performance of the composition based on the average magnitude of the storage modulus;
wherein the crosslinked polycarbonate is a bisphenol-A homopolymer having endcaps derived from 4-hydroxybenzophenone, a bisphenol-A copolymer having co-monomers derived from 4,4'-dihydroxybenzophenone, or a combination thereof.

2. The method of claim 1, wherein the flame performance is determined by comparing the average magnitude of the storage modulus to a reference table.

3. The method of claim 1, wherein the flame performance is determined by comparing the average magnitude of the storage modulus to a threshold value.

4. The method of claim 1, wherein the temperature range over which the average magnitude is determined is at least 10° C.

5. The method of claim 1, wherein the temperature range over which the average magnitude is determined is at least 30° C.

6. A method for selecting a crosslinkable polycarbonate that will achieve UL94 5VA performance at a thickness of 1.5 mm, comprising:
molding a part from a composition comprising a crosslinkable polycarbonate resin that contains an aromatic ketone-containing moiety derived from a dihydroxy compound or a monohydroxy compound, and a fixed amount of a flame retardant, and a fixed amount of a cyclic siloxane;
exposing the molded part to ultraviolet light to induce crosslinking; measuring the storage modulus (G') versus temperature of the molded part using dynamic mechanical analysis, the measurement including a rubber plateau of the polycarbonate;
extrapolating an average magnitude of the storage modulus over a temperature range within the rubber plateau; and
selecting the polycarbonate resin if the G' is 5 or greater;
wherein the crosslinked polycarbonate is a bisphenol-A homopolymer having endcaps derived from 4-hydroxybenzophenone, a bisphenol-A copolymer having co-monomers derived from 4,4'-dihydroxybenzophenone, or a combination thereof.

7. The method of claim 6, wherein the temperature range over which the average magnitude is determined is at least 10° C.

8. The method of claim 7, wherein the temperature range over which the average magnitude is determined is at least 30° C.

9. The method of claim 6, wherein the temperature range over which the average magnitude is determined is at least 30° C.

10. A method for selecting a crosslinkable polycarbonate that will achieve UL94 V0 performance at a thickness of 1.2 mm, comprising:
molding a part from a composition comprising a crosslinkable polycarbonate resin that contains an aromatic ketone-containing moiety derived from a dihydroxy compound or a monohydroxy compound, and a fixed amount of a flame retardant additive, and a fixed amount of a cyclic siloxane;
exposing the molded part to ultraviolet light to induce crosslinking;

measuring the storage modulus (G') versus temperature of the molded part using dynamic mechanical analysis, the measurement including a rubber plateau of the polycarbonate;

extrapolating an average magnitude of the storage modulus over a temperature range within the rubber plateau; and selecting the polycarbonate resin if the G' is 9 or greater;

wherein the crosslinked polycarbonate is a bisphenol-A homopolymer having endcaps derived from 4-hydroxybenzophenone, a bisphenol-A copolymer having co-monomers derived from 4,4'-dihydroxybenzophenone, or a combination thereof.

11. The method of claim 10, wherein the temperature range over which the average magnitude is determined is at least 10° C.

* * * * *